(12) United States Patent
Lovell

(10) Patent No.: US 6,395,005 B1
(45) Date of Patent: May 28, 2002

(54) ACETABULAR ALIGNMENT APPARATUS AND METHOD

(75) Inventor: Timothy Patrick Lovell, Spokane, WA (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/549,000

(22) Filed: Apr. 14, 2000

(51) Int. Cl.[7] .................................................. A61F 2/32
(52) U.S. Cl. ...................................... 606/91; 623/22.11
(58) Field of Search .............................. 606/91, 99, 81, 606/102; 623/22.11, 22.23, 22.24, 22.35, 22.36, 22.37

(56) References Cited

U.S. PATENT DOCUMENTS

| | | |
|---|---|---|
| 4,994,064 A | 2/1991 | Aboczky |
| 5,037,424 A | 8/1991 | Aboczsky |
| 5,141,512 A | 8/1992 | Farmer et al. |
| 5,540,697 A | 7/1996 | Rehmann et al. |
| 5,571,111 A | 11/1996 | Aboczky |
| 5,658,294 A | 8/1997 | Sederholm |
| 5,814,050 A | 9/1998 | Benson |

*Primary Examiner*—David O. Reip
*Assistant Examiner*—Julian W. Woo
(74) *Attorney, Agent, or Firm*—Arthur Jacob

(57) ABSTRACT

An acetabular alignment method and apparatus utilize natural landmarks available on a pelvis to guide the alignment of an acetabular device in connection with the implant of a prosthetic hip joint at an implant site in the pelvis. The acetabular device is engaged with a positioning shaft having a longitudinal shaft axis, and locators are mounted upon the positioning shaft for placement adjacent selected landmarks on the pelvis to orient the shaft axis relative to the acetabular axis of a prepared acetabulum at the implant site in order to place the shaft axis at a prescribed angle of abduction and a prescribed angle of anteversion, thereby orienting the acetabular device at the appropriate angle of abduction and the appropriate angle of anteversion.

28 Claims, 6 Drawing Sheets

ACETABULAR ALIGNMENT APPARATUS AND METHOD

BACKGROUND OF THE INVENTION

The present invention relates generally to the alignment of an acetabular device in connection with the implant of a prosthetic hip joint in a natural pelvis and pertains, more specifically, to apparatus and method which utilize internal natural landmarks provided by the pelvis itself to guide the appropriate alignment of the acetabular device at an implant site in the pelvis.

Currently available acetabular alignment apparatus and procedures generally rely upon either the use of reference locations external to the pelvis of a patient, or direct observation of an implant site by a surgeon during a prosthetic hip joint implant procedure. The reliance upon external references tends to introduce inaccuracies arising from variations in a patient's position on the operating room table. Thus, despite the use of elaborate and expensive equipment in connection with such procedures, reliable and consistent results are not assured. On the other hand, while alignment guides used by surgeons in connection with direct observation techniques are relatively simple and inexpensive, and can expedite the implant procedure, accuracy of alignment depends heavily upon the skill of the surgeon and can vary widely among practitioners in the field.

The present invention provides alignment apparatus and method which rely upon specific anatomic structures available internally at the pelvis to furnish natural landmarks as references for attaining accurate alignment of an acetabular device at an implant site in the pelvis. As such, the present invention attains several objects and advantages, some of which are summarized as follows: Enables more precise alignment of an acetabular device with more reliably consistent accuracy; attains consistent accuracy with a relatively simple, easy-to-use apparatus and method; reduces the likelihood of inaccuracies which might otherwise be introduced by variations in the skills of different surgeons; facilitates an implant procedure, enabling reductions in operating time and patient trauma; provides accurate results without reliance upon elaborate and expensive equipment and procedures; simplifies preliminary preparations as well as the implant procedure itself; reduces the complexity of implant procedures and apparatus, with a concomitant reduction in the expense of such procedures and apparatus; accommodates readily to the specific pelvic anatomic structure of a particular patient for attaining more effective results, better tailored to the requirements of each individual patient; reduces the likelihood of inaccuracies which might otherwise be introduced by variations in a patient's position on the operating room table; instills increased confidence in both surgeons and patients toward completion of a procedure effective to attain a desirable end result; is available for effective use in connection with a variety of acetabular devices; enables an increase in the effective service life of an implanted hip prosthesis by increasing accuracy in the alignment of component parts of the implant; provides an alignment apparatus of rugged construction, capable of reliable performance over a long service life.

The above objects and advantages, as well as further objects and advantages, are attained by the present invention which may be described briefly as an alignment apparatus for use in connection with the implant of a hip prosthesis at an implant site within a pelvis for aligning an acetabular device within the pelvis about an axis of abduction and an axis of anteversion passing through a center of rotation on an acetabular axis at the implant site, the acetabular axis, the axis of abduction and the axis of anteversion being mutually perpendicular, the pelvis including a first natural landmark located essentially in a first anatomical plane containing the axis of abduction and oriented at a known angle of abduction, the first natural landmark being spaced from the center of rotation along a first anatomical line extending between the center of rotation and the first natural landmark, and a second natural landmark located essentially in a second anatomical plane containing the axis of anteversion and oriented at a known angle of anteversion, the second natural landmark being spaced from the center of rotation along a second anatomical line extending between the center of rotation and the second natural landmark, the second anatomical line making an anatomical angle with the first anatomical line, the acetabular device having a polar axis and a device center of rotation, the alignment apparatus serving to orient the polar axis at a prescribed angle of abduction and a prescribed angle of anteversion, the alignment apparatus comprising: a positioning shaft for engaging the acetabular device, the positioning shaft having a first end, a second end, a known reference location, and a shaft axis extending longitudinally between the first and second ends of the positioning shaft for following a given direction relative to the polar axis of the acetabular device when the positioning shaft is engaged with the acetabular device, with the acetabular device placed relative to the known reference location on the positioning shaft and the shaft axis extending through the device center of rotation, and the second end of the positioning shaft located remote from the acetabular device; a first locator; a first mount coupling the first locator with the positioning shaft for enabling selective relative movement between the first locator and the known reference location along a first locator direction spaced laterally from the shaft axis and lying within a first alignment plane containing the shaft axis, such that upon selection of a predetermined location of the first locator along the first locator direction, relative to the known reference location, engagement of the first locator with the pelvis adjacent the first natural landmark will place the shaft axis in an orientation corresponding to the prescribed angle of abduction; a second locator; and a second mount coupling the second locator with the positioning shaft for enabling selective relative movement between the second locator and the known reference location along a second locator direction spaced laterally from the shaft axis and lying within a second alignment plane containing the shaft axis, the second alignment plane making an alignment angle with the first alignment plane, the alignment angle corresponding essentially to the anatomical angle between the first and second anatomical lines, such that upon selection of a predetermined location of the second locator along the second locator direction, relative to the known reference location, engagement of the second locator with the pelvis adjacent the second natural landmark will place the shaft axis in an orientation corresponding to the prescribed angle of anteversion.

In addition, the invention includes a method for use in connection with the implant of a hip prosthesis at an implant site within a pelvis for aligning an acetabular device within the pelvis about an axis of abduction and an axis of anteversion passing through a center of rotation on an acetabular axis at the implant site, the acetabular axis, the axis of abduction and the axis of anteversion being mutually perpendicular, the pelvis including a first natural landmark located essentially in a first anatomical plane containing the axis of abduction and oriented at a known angle of abduction, the first natural landmark being spaced from the center of rotation along a first anatomical line extending between the center of rotation and the first natural landmark, and a second natural landmark located essentially in a second anatomical plane containing the axis of anteversion and oriented at a known angle of anteversion, the second natural landmark being spaced from the center of rotation along a second anatomical line extending between the center of rotation and the second natural landmark, the second anatomical line making an anatomical angle with the first anatomical line, the acetabular device having a polar axis and a device center of rotation, the method serving to orient the polar axis at a prescribed angle of abduction and a prescribed angle of anteversion, the method comprising: establishing a first locator point lying in a first alignment plane containing the polar axis of the acetabular device, the first locator point being in a first locator position relative to the polar axis and the device center of rotation, spaced a lateral distance from the polar axis and located at a prescribed longitudinal location relative to the device center of rotation; establishing a second locator point lying in a second alignment plane containing the polar axis of the acetabular device, the second alignment plane making an alignment angle with the first alignment plane, the alignment angle corresponding essentially to the anatomical angle between the first and second anatomical lines, the second locator point being at a second locator position spaced a lateral distance from the polar axis and located at a prescribed longitudinal position from the device center of rotation; placing the acetabular device at the implant site with the device center of rotation coincident with the center of rotation on the acetabular axis; orienting the first alignment plane so as to include the first anatomical line within the first alignment plane; placing the first locator point adjacent the first natural landmark while the first alignment plane is oriented so as to include the first anatomical line within the first alignment plane to orient the polar axis at the prescribed angle of abduction; orienting the second alignment plane so as to include the second anatomical line within the second alignment plane; and placing the second locator point adjacent the second natural landmark while the second alignment plane is oriented so as to include the second anatomical line within the second alignment plane to orient the polar axis at the prescribed angle of anteversion.

The invention will be understood more fully, while still further objects and advantages will become apparent, in the following detailed description of preferred embodiments of the invention illustrated in the accompanying drawing, in which:

DETAILED DESCRIPTION OF THE INVENTION

Figure 1:
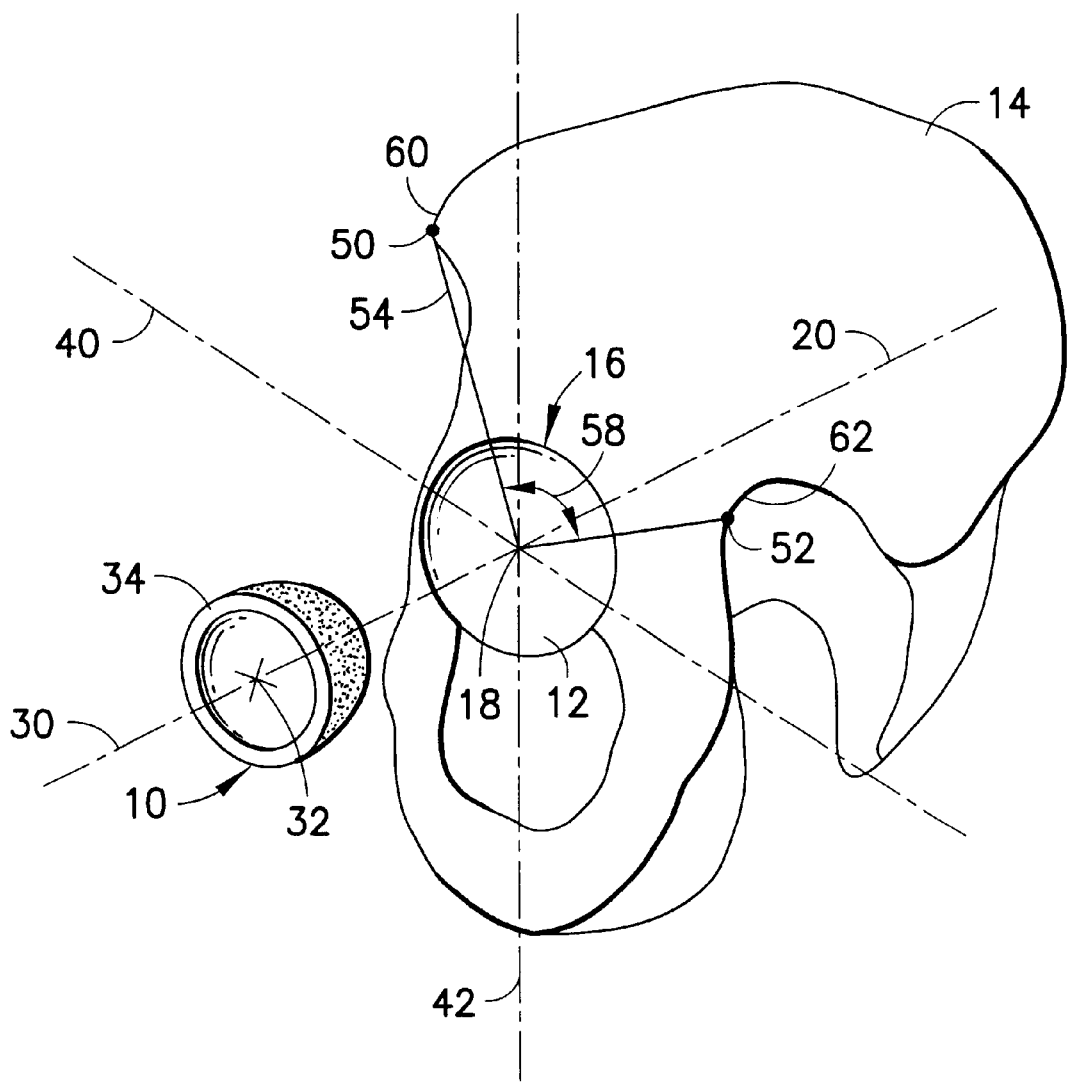
FIG. 1 is a partially diagrammatic, exploded pictorial perspective view showing an acetabular device being implanted at an implant site in a pelvis.

Referring now to the drawing, and especially to FIG. 1 thereof, an acetabular device is illustrated in the form of an acetabular cup 10 shown being placed at a prepared acetabulum 12 in a natural pelvis 14 in connection with the implant of a hip prosthesis at an implant site 16. The prepared acetabulum 12 has a center of rotation 18 on an acetabular axis 20, and the acetabular cup 10 has a polar axis 30 passing through the center of rotation 32 of the acetabular cup 10, and a face 34. The acetabular cup 10 is to be aligned so that the polar axis 30 is oriented at a prescribed angle of abduction and at a prescribed angle of anteversion relative to the acetabular axis 20 when the acetabular cup 10 is implanted within the pelvis 14 at the implant site 16. The angle of abduction denotes the degree to which the acetabular cup 10 is rotated about an axis of abduction 40 passing through the center of rotation 18 and extending in a generally anterior-posterior direction, and the angle of anteversion denotes the degree to which the acetabular cup 10 is rotated about an axis of anteversion 42 passing through the center of rotation 18 and extending in a generally superior-inferior direction, normal to the axis of abduction 40. The acetabular axis 20, the axis of abduction 40 and the axis of anteversion 42 are mutually perpendicular, establishing orthogonal coordinates for defining the orientation of the acetabular cup 10 when implanted at the implant site 16.

The pelvis 14 includes a number of identifiable pelvic anatomic structures providing natural landmarks which can serve as reference locations for determining the desired alignment of the polar axis of an acetabular device placed at an implant site in the pelvis. The present invention relies upon the selection of two of these natural landmarks, the selected first natural landmark 50 being located essentially in a first anatomical plane containing the axis of abduction 40, and the selected second natural landmark 52 being located essentially in a second anatomical plane containing the axis of anteversion 42. The angle of abduction of the first anatomical plane and the angle of anteversion of the second anatomical plane can be determined clinically for each selected natural landmark, so that the orientation of the first anatomical plane for a selected first natural landmark is known in terms of abduction, and the orientation of the second anatomical plane for a selected second natural landmark is known in terms of anteversion. The first natural landmark 50 is spaced at a first distance from the center of rotation 18 along a first anatomical line 54 lying in the first anatomical plane and extending between the first natural landmark 50 and the center of rotation 18, and the second natural landmark 52 is spaced at a second distance from the center of rotation 18 along a second anatomical line 56 lying in the second anatomical plane and extending between the second natural landmark 52 and the center of rotation 18, the second anatomical line 56 making an anatomical angle 58 with the first anatomical line 54. For the purposes of describing preferred embodiments of the present invention, the first natural landmark 50 is provided by an anterior superior iliac spine 60, and the second natural landmark 52 is provided by the corresponding greater sciatic notch 62. The anterior superior iliac spine 60 and the greater sciatic notch 62 have a consistent, reproducible relationship to the acetabulum 12 with respect to the direction of the first anatomical line 54 as related to abduction, the direction of the second anatomical line 56 as related to anteversion, and the anatomical angle 58 between the lines 54 and 56. Thus, utilizing the anterior superior iliac spine 60 and the greater sciatic notch 62 for the location of the first and second natural landmarks 50 and 52, the anatomical angle 58, though slightly different in male patients as opposed to female patients, is approximately 90°.

Figure 2:
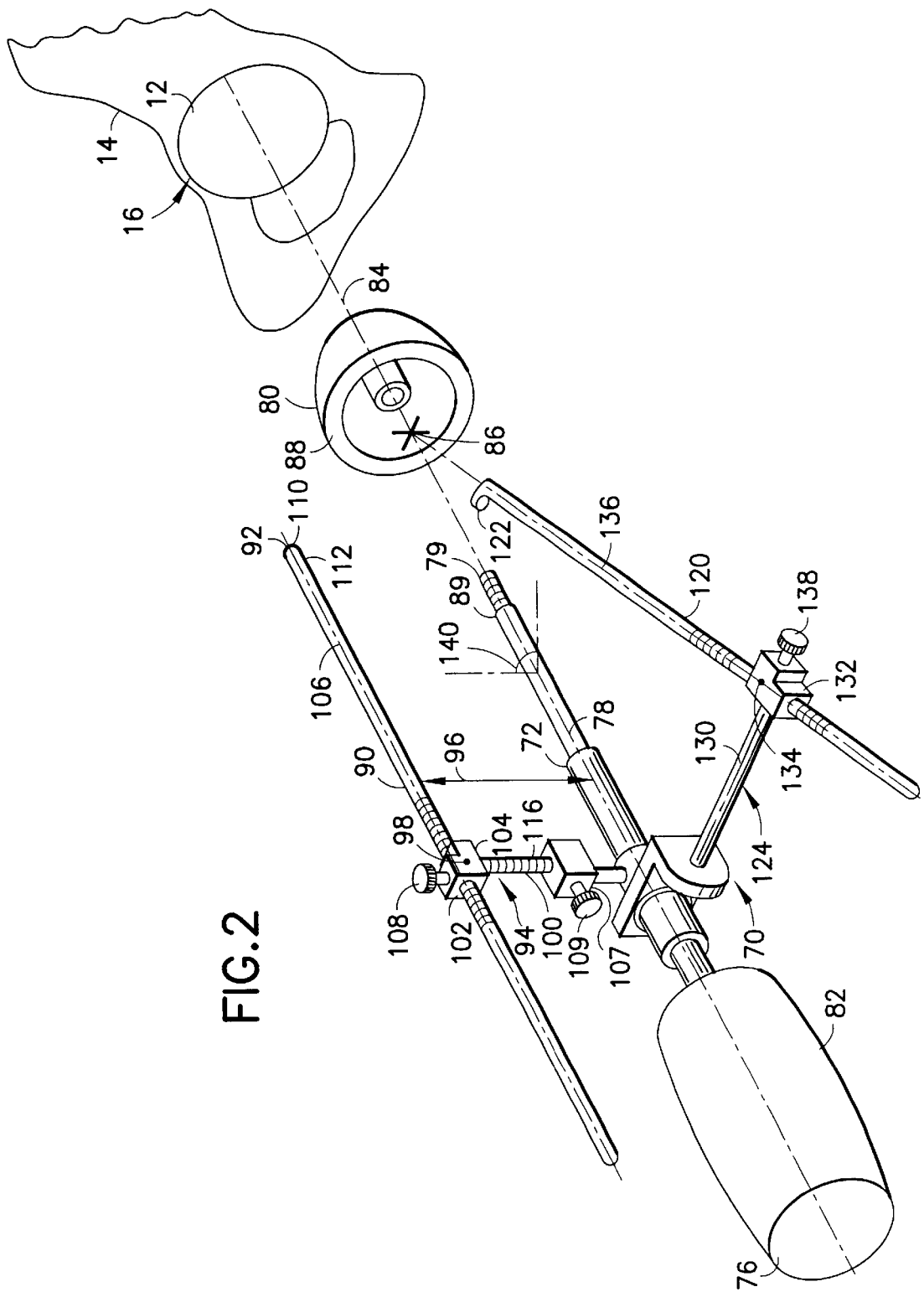
FIG. 2 is an exploded pictorial perspective view showing an acetabular device being oriented at an implant site in a pelvis, utilizing apparatus and method in accordance with the present invention.
Figure 3:
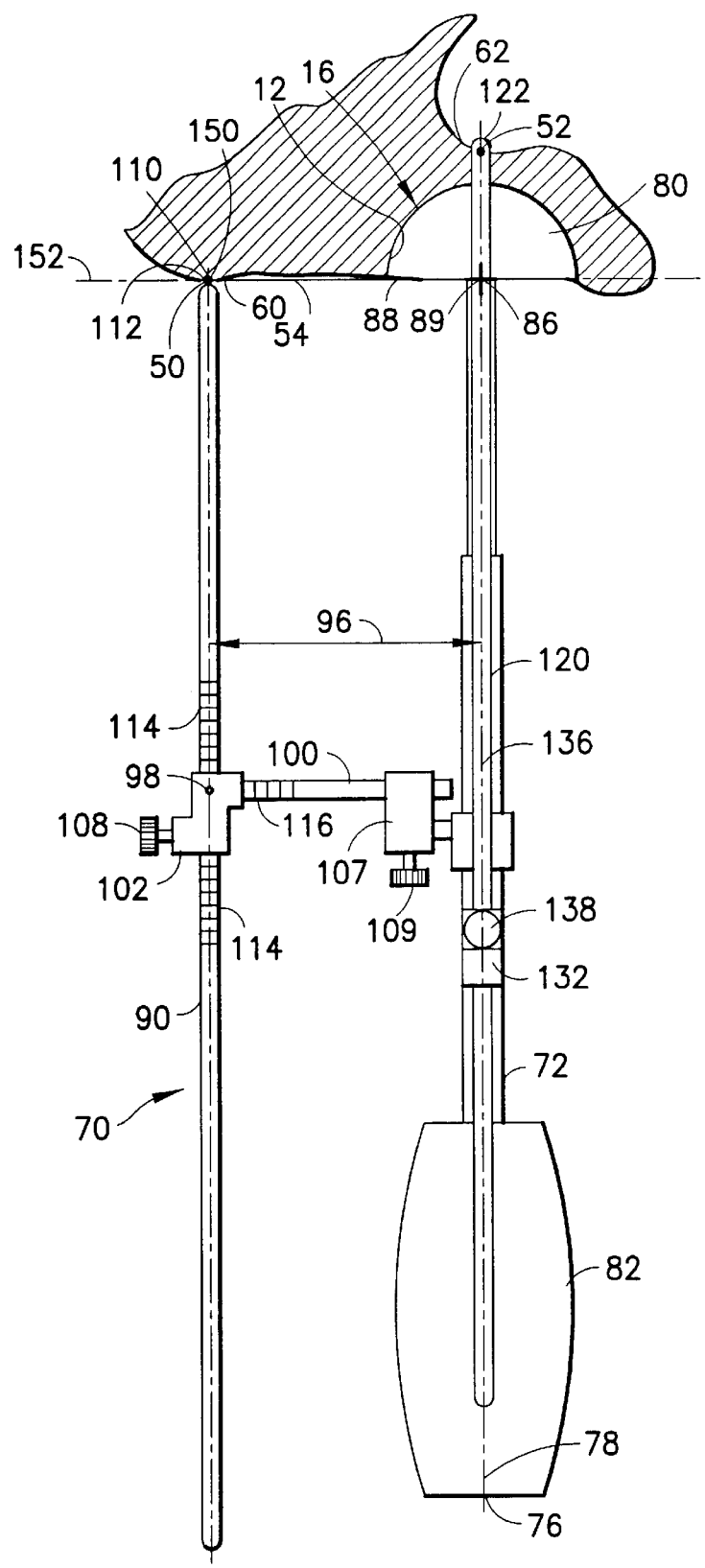
FIG. 3 is an elevational view illustrating the apparatus and method depicted in FIG. 2.
Figure 4:
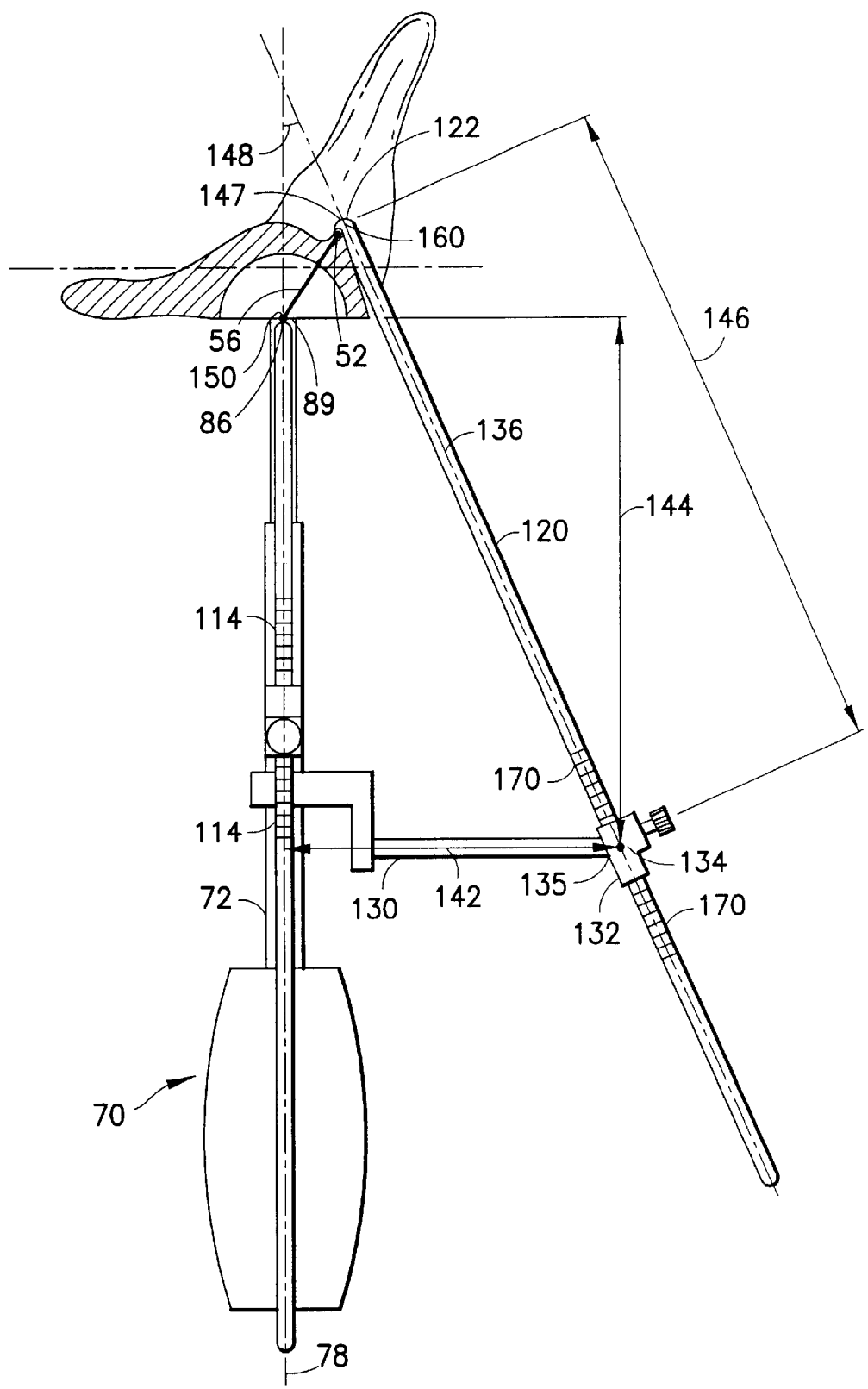
FIG. 4 is a plan view illustrating the apparatus and method.

Turning now to FIGS. 2 through 4, an alignment apparatus constructed in accordance with the present invention is illustrated generally at 70 and is seen to include a positioning shaft 72 having a first end 74, a second end 76, and a shaft axis 78 extending longitudinally along the positioning shaft 72 between the first and second ends 74 and 76. A threaded coupling 79 at the first end 74 engages and secures an acetabular device, here shown in the form of a trial component 80, at the first end 74, and a manipulating handle 82 is located at the second end 76, remote from the trial component 80. The trial component 80 simulates the acetabular cup 10 and includes a polar axis 84 passing through a center of rotation 86, and a face 88, all corresponding to the polar axis 30, center of rotation 32 and face 34 of the acetabular cup 10. The threaded coupling 79 couples the trial component 80 with the positioning shaft 72 so that the shaft axis 78 follows a given direction relative to the polar axis 84 of the trial component 80. The shaft axis 78 passes through the center of rotation 86 of the trial component 80, and the center of rotation 86 is placed relative to a known reference location 89 along the shaft axis 78. In the illustrated embodiment, the known reference location 89 is shown coincident with the center of rotation 86 when the trial component 80 is secured to the positioning shaft 72.

A first locator includes a first locator rod 90 having a first locator end 92 and coupled with the positioning shaft 72 by a first mount 94 which locates the locator rod 90 at a first mounting location placed at a lateral distance 96 from the shaft axis 78 and spaced a longitudinal distance from the reference location 89 to establish a first reference location 98. The first mount 94 includes a first arm 100 secured to the positioning shaft 72 at a longitudinal position along the shaft axis 78, the longitudinal position being at a known longitudinal distance from the known reference location 89 toward the second end 76 of the positioning shaft 72, with the first arm 100 having a first arm length extending generally perpendicular to the shaft axis 78. A first coupling 102 at a remote end 104 of the first arm 100 is placed at the first reference location 98 and couples the locator rod 90 for selective sliding movement along a first locator direction 106 relative to the first reference location 98, and relative to the known reference location 89, and a further coupling 107 couples the first arm 100 with the positioning shaft 72 to enable selective changes in the arm length for selection of the lateral distance 96, to place the reference location 98 at a prescribed lateral distance from the shaft axis 78, thereby locating the first locator end 92 at a selected location in a first alignment plane containing the shaft axis 78, which first alignment plane is the plane of the paper in FIG. 3, and set screws 108 and 109 selectively secure the locator rod 90 in place within the respective couplings 102 and 107. In the illustrated embodiment, the locator end 92 includes an abutment 110 placed at an end tip 112 of the locator rod 90, for purposes to be described below, and calibrated indices 114 and 116 are placed on the locator rod 90 and on the arm 100, respectively, to provide an indication of the selected location of the first locator end 92.

A second locator includes a second locator rod 120 having a second locator end 122 and coupled with the positioning shaft 72 by a second mount 124 which locates the locator rod 120 at a second mounting location placed at a lateral distance from the shaft axis 78. The second mount 124 includes a second arm 130 secured to the positioning shaft 72 at a longitudinal position along the shaft axis 78, spaced longitudinally from the known reference location 89 toward the second end 76 of the positioning shaft 72, with the second arm 130 having a second arm length and extending generally perpendicular to the shaft axis 78. A second coupling 132 is placed at a second reference location, illustrated in the form of a fixed location 134, at remote end 135 of the second arm 130, and couples the locator rod 120 for selective sliding movement along a second locator direction 136 relative to the fixed location 134, and relative to the known reference location 89, for locating the second locator end 122 at a selected position in a second alignment plane containing the shaft axis 78, which second alignment plane is illustrated as the plane of the paper in FIG. 4 and makes an alignment angle 140 with the first alignment plane. A set screw 138 selectively secures the locator rod 120 in place within the coupling 132. The fixed location 134 is placed at a prescribed lateral distance 142 from the shaft axis 78 and at a prescribed longitudinal distance 144 from the known reference location 89 and, hence, from the center of rotation 86 of the trial component 80, and sliding movement of the locator rod 120 relative to coupling 132 along the locator direction 136 places the selected position of the second locator end 122 at a selectable distance 146 from the fixed location 134. In the illustrated embodiment, locator end 122 includes a grip in the form of a hook-like finger 147 placed at the locator end 122, and the locator direction 136 makes an acute angle 148 with the shaft axis 78 for purposes to be described below.

Alignment of the trial component 80 is accomplished by securing the trial component 80 at the first end 74 of the positioning shaft 72, as shown in FIGS. 3 and 4. The trial component 80 is located in a fixed position relative to the known reference location 89, the known reference location 89 being shown coincident with the center of rotation 86 of the trial component 80. A first locator point 150 is established in the first alignment plane by selecting the lateral distance 96 and sliding the first locator rod 90 relative to the first coupling 102 to move the end tip 112 to a predetermined position relative to the polar axis 84 and the center of rotation 86 of the trial component 80. The set screws 108 and 109 then are actuated to lock the first locator rod 90 against further movement, fixing the predetermined position of the end tip 112. In this instance, the predetermined position of the end tip 112 is within a further plane 152 containing the face 88 of the trial component 80, which further plane 152 is shown perpendicular to the plane of the paper in FIG. 3. With the trial component 80 seated at the implant site 16, the first alignment plane is oriented so as to include the first anatomical line 54 within the first alignment plane and the alignment apparatus 70 is rotated about the axis of abduction 40, 10 utilizing the manipulating handle 82, until the abutment 110 of the end tip 112 is moved to the first anatomical plane, placing the first locator point 150 essentially at the first natural landmark 50 provided by the anterior superior iliac spine 60, with the end tip 112 being placed essentially against the anterior superior iliac spine 60, as illustrated in FIG. 3. It has been determined clinically that the first anatomical plane, containing the anterior superior iliac spine, lies at the desired prescribed angle of abduction. Accordingly, such placement of the end tip 112, at the first location point 150, orients the polar axis 84 of the trial component 80 at the prescribed angle of abduction.

With the alignment angle 140 between the first and second alignment planes of the alignment apparatus 70 set to correspond to the anatomical angle 58 which, in this instance, is approximately 90°, the second alignment plane is oriented to include the second anatomical line 56 and the hook-like finger 147 at the locator end 122 of the second locator rod 120 is placed so as to grip the pelvis 14 essentially at the greater sciatic notch 62, thereby establishing a second locator point 160 spaced at the selectable distance 146 from the fixed location 134, the second locator point 160 thus being placed essentially in the second anatomical plane and adjacent the second natural landmark 52. Selection of the distance 146 along the locator direction 136 between the fixed location 134 and the locator end 122, when the locator end 122 is placed adjacent the second natural landmark 52, as illustrated in FIG. 4, determines the rotational position of the shaft axis 78 of the positioning shaft 72 about the axis of anteversion 42 and, consequently, the orientation of the polar axis 84 of the trial component 80 about the axis of anteversion 42. Selection of the distance 146 is accomplished by sliding the second locator rod 120 relative to the second coupling 132 until a predetermined distance 146 is indicated by calibrated indices 170 placed on the locator rod 120, and then locking the second locator rod 120 in place, relative to the second coupling 132, by means of the set screw 138. Since the orientation of the second anatomical plane, containing the greater sciatic notch 62, is known in terms of anteversion, selection of the appropriate predetermined distance 146 orients the polar axis 84 of the trial component 80 at the prescribed angle of anteversion.

Figure 5:
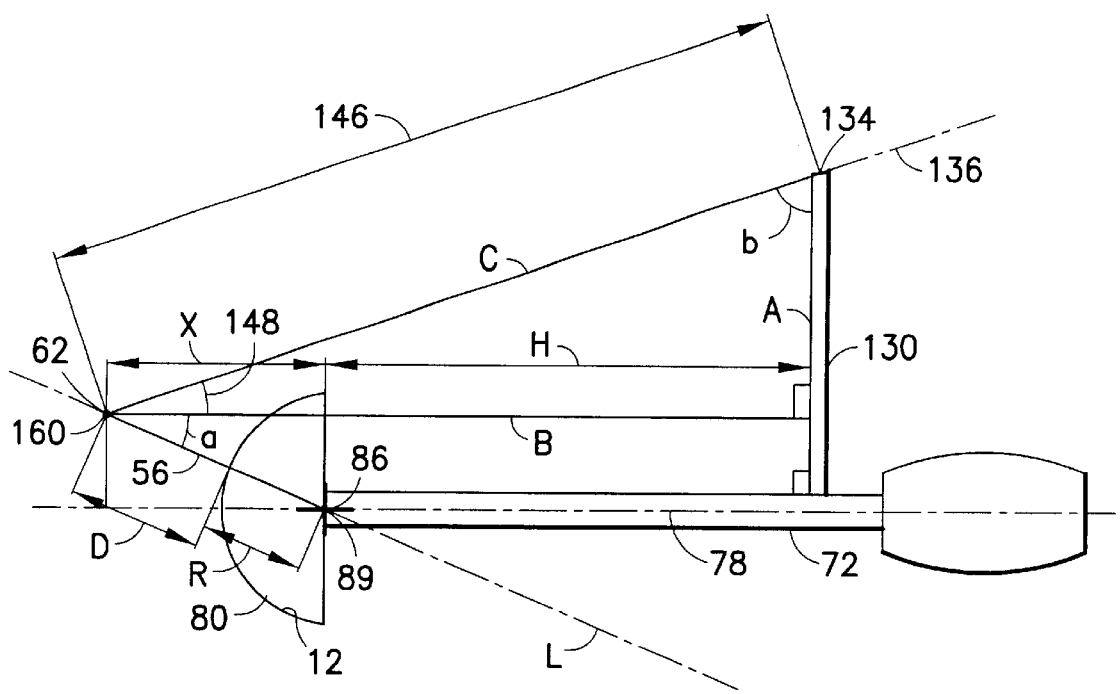
FIG. 5 is a diagram showing the derivation of the value of a particular parameter utilized in the method.

The predetermined distance 146 is arrived at by a calculation illustrated in connection with FIG. 5, wherein the relative positions of the positioning shaft 72, with the trial component 80 secured thereto, and the greater sciatic notch 62 are shown diagrammatically in the second alignment plane. In the diagram of FIG. 5, the trial component 80 is oriented in a prescribed angle of anteversion which, in this instance, has been selected by the surgeon to be an angle of 15°. The line L, which lies along the second anatomical line 56, passes through the greater sciatic notch 62 and the center of rotation 86 of the trial component 80, which center of rotation 86 is coincident with the center of rotation 18 of the prepared acetabulum 12. It has been determined clinically that an acetabular device placed so that the polar axis of the acetabular device lies along line L is in approximately 40° of anteversion. The distance D is the shortest distance between the prepared acetabulum 12 and the greater sciatic notch 62 and is determined by a measurement taken along line L. The distance R is the radius of the acetabular device, in this instance the radius of the trial component 80.

With the trial component 80 oriented at the prescribed angle of anteversion of 15°, a right triangle is formed having sides A, B and hypotenuse C. Side A lies along the second arm 130 which is perpendicular to the shaft axis 78 of the positioning shaft 72. Side B is the sum of the known longitudinal distance H, determined by the longitudinal position of the second arm 130 along the shaft axis 78 relative to the center of rotation 86 of the trial component 80, which center of rotation 86 is coincident with the known reference location 89, is placed at the center of rotation 18 of the prepared acetabulum 12 and is located on the axis of anteversion 42, and a further longitudinal distance X extending to the greater sciatic notch 62. The angle b is an acute angle which is complementary to acute angle 148 between the second locator direction 136 and the shaft axis 78 and is known as a result of the placement of the fixed location 134. In this instance, angle b equals 640. The angle a is a correction angle between the angle of anteversion along line L which, for the choice of greater sciatic notch 62 as the second natural landmark 52, is 40°, and the desired angle of anteversion which, in this instance, is selected to be 15°. Thus, the length of the hypotenuse C, which is the predetermined distance 146 between the locator point 160 and the fixed location 134 for the prescribed angle of anteversion of 15°, can be calculated, as follows:

$$C = \frac{H + X}{\mathrm{SIN}64°}$$

where $$x = (D+R)\cos a$$

and $$a = 40° - 15° = 25°$$

so that $$C = \frac{H + (D+R)\mathrm{COS}25°}{\mathrm{SIN}64°}$$

By setting the predetermined distance 146 to the length of hypotenuse C, as calculated above, the trial component 80 is aligned at the prescribed 15° angle of anteversion.

The predetermined distance 146 is selected by moving the second locator end 122 along the second locator direction 136, relative to the fixed location 134. To that end, second locator rod 120 is moved along the second locator direction 136 by sliding the second locator rod 120 within the second coupling 132 until the indices 170 indicate the calculated distance. The second locator rod 120 then is locked in place by actuating the set screw 138. With the end tip 112 of the first locator rod 90 placed at the anterior superior iliac spine 60, and the hook-like finger 147 placed at the greater sciatic notch 62, as described above, the trial component 80 is aligned to the prescribed angle of abduction and the prescribed angle of anteversion, independent of the position of the patient, any pelvic tilt or other external factors.

The trial component 80 then is removed from the first end 74 of the positioning shaft 72 of the alignment apparatus 70 and is replaced by the acetabular cup 10. With the settings of the first and second locator rods 90 and 120 unchanged, the acetabular cup 10 is placed within the prepared acetabulum 12, aligned to the prescribed angle of abduction and the prescribed angle of anteversion. If desired in connection with a particular implant procedure, the acetabular cup 10 itself may be aligned without the necessity of conducting a previous alignment of a trial component 80, utilizing the same apparatus and procedure outlined above, but with the positioning shaft 72 engaged with the acetabular cup 10 instead of with a trial component 80.

The sequence of steps in the procedure may be varied without departing from the basic method of the present invention. Thus, while in the above-outlined procedure the described sequence of steps calls for placing the acetabular device (attached to the alignment apparatus) in the prepared acetabulum, then setting the prescribed angle of abduction by rotating the alignment apparatus 70 about the axis of abduction 40 until the end tip 112 is placed adjacent the anterior superior iliac spine 60, and then selecting the distance between the fixed location 134 and the hook-like finger 147 to rotate the alignment apparatus 70 about the axis of anteversion 42 for setting the prescribed angle of anteversion, the sequence of steps can be rearranged without affecting the end result. For example, the prescribed angle of anteversion can be set before setting the prescribed angle of abduction. Further, either one or both of the first and second locator points 150 and 160 can be placed at a corresponding locator position either before or after placement of the acetabular device in the prepared acetabulum 12. In this manner, the surgeon is able to pre-set the alignment apparatus if so desired.

Figure 6:
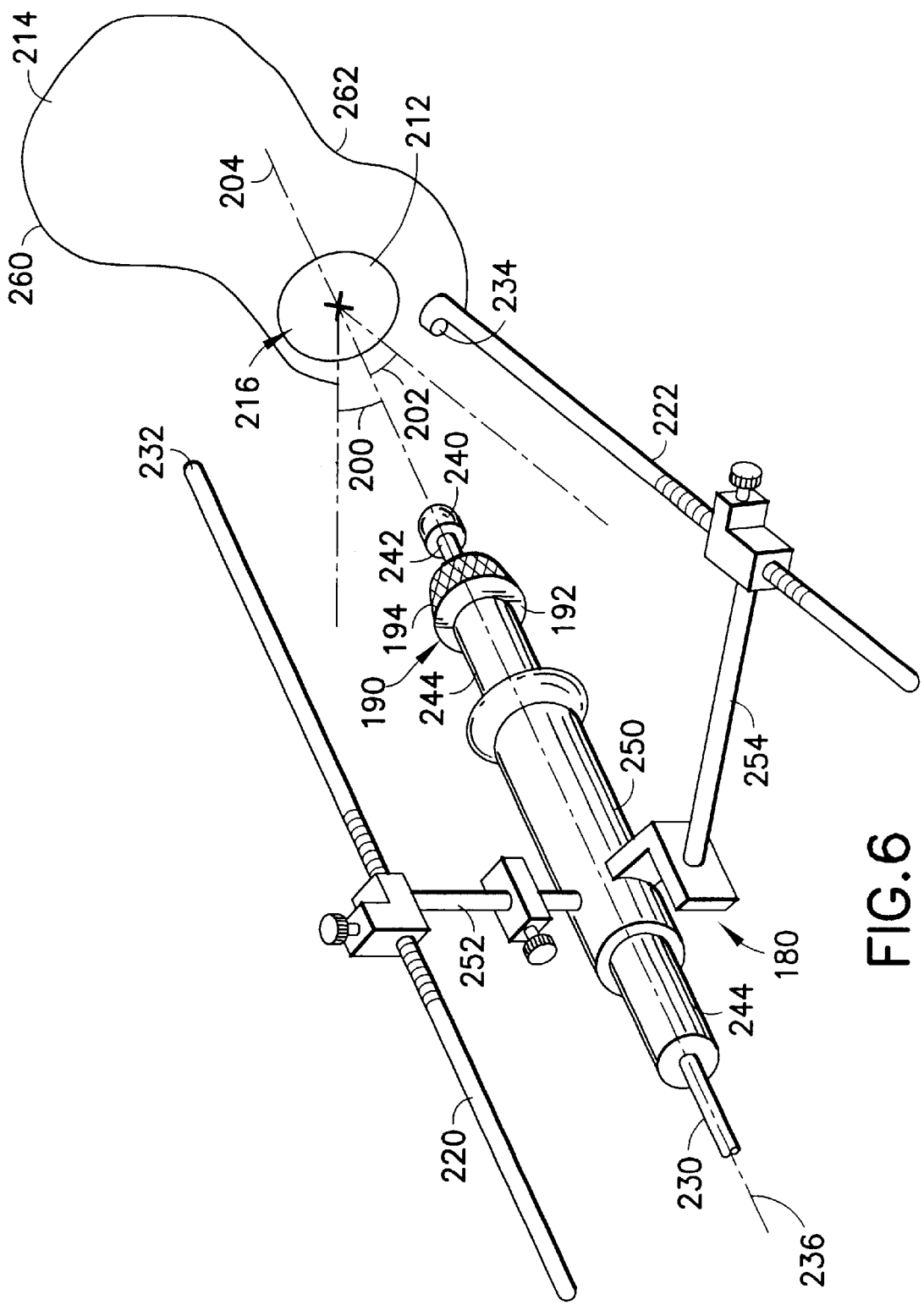
FIG. 6 is a pictorial perspective view similar to FIG. 2, and showing another embodiment of the apparatus and method of the invention utilized in connection with another acetabular device.

Turning now to FIG. 6, another alignment apparatus 180 is constructed in accordance with the present invention and is shown aligning a acetabular device in the form of a reamer 190 having a cutter 192 with a frusto-conical cutting surface 194 which must be aligned at a prescribed angle of abduction 200 and a prescribed angle of anteversion 202, relative to the acetabular axis 204 of a partially prepared acetabulum 212, in order to complete the preparation of the acetabulum for the reception of an acetabular cup of the type which requires an appropriately oriented complementary frusto-conical seat in the pelvis 214 at the implant site 216.

Alignment apparatus 180 is similar to previously described alignment apparatus 70 in that first and second locator rods 220 and 222 are spaced laterally from a longitudinally extending positioning shaft 230 and include respective locator ends 232 and 234 for orienting the shaft axis 236 at the prescribed angle of abduction 200 and at the prescribed angle of anteversion 202, in the same manner as described in connection with alignment apparatus 70. In the present embodiment, however, the alignment apparatus includes a semi-spherical pilot 240 affixed at the first end 242 of the positioning shaft 230, and the cutter 192 is driven by a tubular drive shaft 244 which is coaxial with the shaft axis 236 and which is journaled for rotation on the positioning shaft 230 and is mounted for axial sliding movement along the positioning shaft 230. An outer sleeve 250 carries the arms 252 and 254 which mount the locator rods 220 and 222 for establishing the appropriate locator points, as described above in connection with alignment apparatus 70. Placement of the pilot 240 in the partially prepared acetabulum 212, and manipulation of the alignment apparatus 180 to orient the shaft axis 236 relative to the acetabular axis 204, utilizing the natural landmarks provided by the anterior superior iliac spine 260 and the corresponding greater sciatic notch 262, as described above, attains the appropriate orientation of the cutting surface 194 for advancement of the cutter 192 along the positioning shaft 230 to the implant site 216 for completing the preparation of the acetabulum.

It will be seen that the present invention attains the several objects and advantages summarized above, namely: Enables more precise alignment of an acetabular device with more reliably consistent accuracy; attains consistent accuracy with a relatively simple, easy-to-use apparatus and method; reduces the likelihood of inaccuracies which might otherwise be introduced by variations in the skills of different surgeons; facilitates an implant procedure, enabling reductions in operating time and patient trauma; provides accurate results without reliance upon elaborate and expensive equipment and procedures; simplifies preliminary preparations as well as the implant procedure itself; reduces the complexity of implant procedures and apparatus, with a concomitant reduction in the expense of such procedures and apparatus; accommodates readily to the specific pelvic anatomic structure of a particular patient for attaining more effective results, better tailored to the requirements of each individual patient; reduces the likelihood of inaccuracies which might otherwise be introduced by variations in a patient's position on the operating room table; instills increased confidence in both surgeons and patients toward completion of a procedure effective to attain a desirable end result; is available for effective use in connection with a variety of acetabular devices; enables an increase in the effective service life of an implanted hip prosthesis by increasing accuracy in the alignment of component parts of the implant; provides an alignment apparatus of rugged construction, capable of reliable performance over a long service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An alignment apparatus for use in connection with the implant of a hip prosthesis at an implant site within a pelvis for aligning an acetabular device within the pelvis about an axis of abduction and an axis of anteversion passing through a center of rotation on an acetabular axis at the implant site, the acetabular axis, the axis of abduction and the axis of anteversion being mutually perpendicular, the pelvis including a first natural landmark located essentially in a first anatomical plane containing the axis of abduction and oriented at a known angle of abduction, the first natural landmark being spaced from the center of rotation along a first anatomical line extending between the center of rotation and the first natural landmark, and a second natural landmark located essentially in a second anatomical plane containing the axis of anteversion and oriented at a known angle of anteversion, the second natural landmark being spaced from the center of rotation along a second anatomical line extending between the center of rotation and the second natural landmark, the second anatomical line making an anatomical angle with the first anatomical line, the acetabular device having a polar axis and a device center of rotation, the alignment apparatus serving to orient the polar axis at a prescribed angle of abduction and a prescribed angle of anteversion, the alignment apparatus comprising:

a positioning shaft for engaging the acetabular device, the positioning shaft having a first end, a second end, a known reference location, and a shaft axis extending longitudinally between the first and second ends of the positioning shaft for following a given direction relative to the polar axis of the acetabular device when the positioning shaft is engaged with the acetabular device, with the acetabular device placed relative to the known reference location on the positioning shaft and the shaft axis extending through the device center of rotation, and the second end of the positioning shaft located remote from the acetabular device;

a first locator;

a first mount coupling the first locator with the positioning shaft for enabling selective relative movement between the first locator and the known reference location along a first locator direction spaced laterally from the shaft axis and lying within a first alignment plane containing the shaft axis, such that upon selection of a predetermined location of the first locator along the first locator direction, relative to the known reference location, engagement of the first locator with the pelvis adjacent the first natural landmark will place the shaft axis in an orientation corresponding to the prescribed angle of abduction;

a second locator; and a second mount coupling the second locator with the positioning shaft for enabling selective relative movement between the second locator and the known reference location along a second locator direction spaced laterally from the shaft axis and lying within a second alignment plane containing the shaft axis, the second alignment plane making an alignment angle with the first alignment plane, the alignment angle corresponding essentially to the anatomical angle between the first and second anatomical lines, such that upon selection of a predetermined location of the second locator along the second locator direction, relative to the known reference location, engagement of the second locator with the pelvis adjacent the second natural landmark will place the shaft axis in an orientation corresponding to the prescribed angle of anteversion.

2. The invention of claim 1 wherein the first natural landmark is provided by an anterior superior iliac spine, the first locator includes a first locator rod having a first locator end and an abutment at the first locator end for abutting the pelvis at the anterior superior iliac spine, a first reference location is placed at a lateral distance from the shaft axis, and the first mount couples the first locator rod with the positioning shaft at the first reference location.

3. The invention of claim 2 wherein the abutment includes an end tip on the first locator rod.

4. The invention of claim 3 wherein the first mount includes a first coupling at the first reference location, the first coupling enabling selective movement of the first locator rod relative to the first reference location, along the first locator direction, for selecting the predetermined location of the first locator.

5. The invention of claim 1 wherein the second natural landmark is provided by a greater sciatic notch, the second mount couples the second locator with the positioning shaft at a second reference location placed at a predetermined longitudinal distance from the known reference location and a predetermined lateral distance from the shaft axis, and the second locator direction makes an acute angle with the shaft axis.

6. The invention of claim 5 wherein the second locator includes a second locator rod having a second locator end, and a grip at the second locator end for gripping the pelvis to secure the second locator end adjacent the greater sciatic notch.

7. The invention of claim 6 wherein the grip includes a hook-like finger at the second locator end.

8. The invention of claim 5 wherein the second locator includes a second locator rod having a second locator end, and including a second coupling at the second reference location, the second coupling enabling selective movement of the second locator rod relative to the second reference location, along the second locator direction, and the predetermined location of the second locator is placed at a predetermined locator distance along the second locator direction between the second locator end and the second reference location.

9. The invention of claim 8 including a grip at the second locator end for gripping the pelvis to secure the second locator end adjacent the greater sciatic notch.

10. The invention of claim 9 wherein the grip includes a hook-like finger at the second locator end.

11. The invention of claim 1 wherein the first natural landmark is provided by an anterior superior iliac spine and the second natural landmark is provided by a corresponding greater sciatic notch, and wherein:

the first locator includes a first locator rod having a first locator end and an abutment at the first locator end for abutting the pelvis at the anterior superior iliac spine, and the first mount couples the first locator rod with the positioning shaft at a first reference location placed at a predetermined lateral distance from the shaft axis; and the second mount includes a second locator rod having a second locator end, the second mount couples the second locator rod with the positioning shaft at a second reference location placed at a predetermined longitudinal distance from the known reference location and a predetermined lateral distance from the shaft axis, and the second locator direction makes an acute angle with the shaft axis.

12. The invention of claim 11 including a grip at the second locator end for gripping the pelvis to secure the second locator end adjacent the greater sciatic notch.

13. The invention of claim 12 wherein the grip includes a hook-like finger at the second locator end.

14. The invention of claim 1 wherein the first mount includes a first arm secured to the positioning shaft and extending generally perpendicular to the shaft axis to a remote end located at a first reference location, the first arm having a first arm length between the first reference location and the remote end, and a first coupling adjacent the remote end coupling the first locator for selective movement relative to the first arm to place and secure the first locator in the predetermined location thereof for establishing the orientation of the shaft axis corresponding to the prescribed angle of abduction.

15. The invention of claim 14 wherein the first locator includes a first locator rod having a first locator end for engaging the pelvis adjacent the first natural landmark.

16. The invention of claim 14 including a second arm secured to the positioning shaft and extending generally perpendicular to the shaft axis from a near end to a far end located at a second reference location, the second arm having a second arm length between the near end and the far end and being approximately orthogonal to the first arm, the second mount including a second coupling adjacent the far end coupling the second locator for selective movement relative to the second reference location to place the second locator in the predetermined location thereof for establishing the orientation of the shaft axis corresponding to the predetermined angle of anteversion.

17. The invention of claim 16 wherein the second locator includes a second locator rod having a second locator end for engaging the pelvis adjacent the second natural landmark.

18. The invention of claim 1 including a manipulating handle at the second end of the positioning shaft.

19. The invention of claim 1 wherein the first natural landmark is provided by an anterior superior iliac spine, the second natural landmark is provided by a corresponding greater sciatic notch, and the anatomical angle is approximately 90°, and wherein the alignment angle is approximately 90° and the first and second planes are approximately orthogonal.

20. A method for use in connection with the implant of a hip prosthesis at an implant site within a pelvis for aligning an acetabular device within the pelvis about an axis of abduction and an axis of anteversion passing through a center of rotation on an acetabular axis at the implant site, the acetabular axis, the axis of abduction and the axis of anteversion being mutually perpendicular, the pelvis including a first natural landmark located essentially in a first anatomical plane containing the axis of abduction and oriented at a known angle of abduction, the first natural landmark being spaced from the center of rotation along a first anatomical line extending between the center of rotation and the first natural landmark, and a second natural landmark located essentially in a second anatomical plane containing the axis of anteversion and oriented at a known angle of anteversion, the second natural landmark being spaced from the center of rotation along a second anatomical line extending between the center of rotation and the second natural landmark, the second anatomical line making an anatomical angle with the first anatomical line, the acetabular device having a polar axis and a device center of rotation, the method serving to orient the polar axis at a prescribed angle of abduction and a prescribed angle of anteversion, the method comprising:

establishing a first locator point lying in a first alignment plane containing the polar axis of the acetabular device, the first locator point being in a first locator position relative to the polar axis and the device center of rotation, spaced a lateral distance from the polar axis and located at a prescribed longitudinal location relative to the device center of rotation;

establishing a second locator point lying in a second alignment plane containing the polar axis of the acetabular device, the second alignment plane making an alignment angle with the first alignment plane, the alignment angle corresponding essentially to the anatomical angle between the first and second anatomical lines, the second locator point being at a second locator position spaced a lateral distance from the polar axis and located at a prescribed longitudinal position from the device center of rotation;

placing the acetabular device at the implant site with the device center of rotation coincident with the center of rotation on the acetabular axis;

orienting the first alignment plane so as to include the first anatomical line within the first alignment plane;

placing the first locator point adjacent the first natural landmark while the first alignment plane is oriented so as to include the first anatomical line within the first alignment plane to orient the polar axis at the prescribed angle of abduction;

orienting the second alignment plane so as to include the second anatomical line within the second alignment plane; and placing the second locator point adjacent the second natural landmark while the second alignment plane is oriented so as to include the second anatomical line within the second alignment plane to orient the polar axis at the prescribed angle of anteversion.

21. The invention of claim 20 the first locator point is placed against the pelvis adjacent the first landmark, and the second locator point is placed against the pelvis adjacent the second landmark.

22. The invention of claim 20 wherein at least one of the first and second locator points is established subsequent to placement of the acetabular device at the implant site.

23. The invention of claim 20 wherein at least one of the first and second locator positions is spaced a selectable distance from a reference location placed at a prescribed lateral distance from the polar axis and a prescribed longitudinal distance from the device center of rotation, and the orientation of the polar axis at a corresponding one of the prescribed angle of abduction and the prescribed angle of anteversion includes selecting the distance between the one of the first and second locator positions and the reference location, while the first and second locator points are placed adjacent the respective first and second natural landmarks, to orient the polar axis at the one of the prescribed angle of abduction and the prescribed angle of anteversion.

24. The invention of claim 20 wherein the second natural landmark is provided by a greater sciatic notch, the second locator position is spaced a selectable distance from a reference location placed at a prescribed lateral distance from the polar axis and a prescribed longitudinal distance from the device center of rotation, the selectable distance between the second locator position and the reference location lying along a locator direction, the locator direction being placed within the second alignment plane and extending at an acute angle to the polar axis, and the polar axis is oriented at the prescribed angle of anteversion by setting the selectable distance to a predetermined distance.

25. The invention of claim 24 including selecting the predetermined distance while the first locator point is placed adjacent the first natural landmark and the second locator point is placed adjacent the second natural landmark.

26. The invention of claim 20 wherein the first natural landmark is provided by an anterior superior iliac spine and the second natural landmark is provided by a corresponding greater sciatic notch, and wherein:

the first locator point is placed against the pelvis adjacent the anterior superior iliac spine, and the second locator point is placed against the pelvis adjacent the corresponding greater sciatic notch; and the second locator position is spaced a selectable distance from a reference location placed at a prescribed lateral distance from the polar axis and a prescribed longitudinal distance from the device center of rotation, the selectable distance between the second locator position and the reference location lying along a locator direction, the locator direction being placed within the second alignment plane and extending at an acute angle to the polar axis, and the polar axis is oriented at the prescribed angle of anteversion by setting the selectable distance to a predetermined distance.

27. The invention of claim 26 wherein the first locator position is located in a further plane essentially normal to the polar axis and passing through the device center of rotation.

28. The invention of claim 26 wherein the alignment angle is approximately 90°.

\* \* \* \* \*